(12) United States Patent
Kaufman et al.

(10) Patent No.: US 9,717,892 B2
(45) Date of Patent: *Aug. 1, 2017

(54) DISPENSING APPLICATOR FOR FLUIDS

(71) Applicant: BIOMED PACKAGING SYSTEMS INC., Norwalk, CT (US)

(72) Inventors: Jack W. Kaufman, Merrick, NY (US); James Brown, Armonk, NY (US)

(73) Assignee: BIOMED PACKAGING SYSTEMS INC., Norwalk, CT (US)

( * ) Notice: Subject to any disclaimer, the term of this patent is extended or adjusted under 35 U.S.C. 154(b) by 114 days.

This patent is subject to a terminal disclaimer.

(21) Appl. No.: 14/556,401

(22) Filed: Dec. 1, 2014

(65) Prior Publication Data
US 2015/0290443 A1    Oct. 15, 2015

Related U.S. Application Data

(63) Continuation of application No. 13/971,425, filed on Aug. 20, 2013, now Pat. No. 8,926,211, which is a continuation of application No. 13/485,013, filed on May 13, 2012, now Pat. No. 8,608,397, which is a continuation of application No. 13/102,973, filed on May 6, 2011, now Pat. No. 8,215,859, which is a continuation of application No. 12/579,728, filed on Oct. 15, 2009, now Pat. No. 7,946,779, which is a continuation of application No. 11/138,142, filed on May 26, 2005, now Pat. No. 7,614,811.

(51) Int. Cl.
| | |
|---|---|
| *B43K 5/14* | (2006.01) |
| *A61F 13/40* | (2006.01) |
| *A61M 35/00* | (2006.01) |
| *B43M 11/06* | (2006.01) |

(52) U.S. Cl.
CPC ........ *A61M 35/006* (2013.01); *A61M 35/003* (2013.01); *B43M 11/06* (2013.01); *A61M 2210/04* (2013.01)

(58) Field of Classification Search
CPC ... A61M 35/003; A61M 35/006; B65D 47/42; B05C 1/06
USPC .......................................... 401/132–134, 183
See application file for complete search history.

(56) References Cited

U.S. PATENT DOCUMENTS 5,054,948 A * 10/1991 Honda ................ A61M 35/006
 401/132

FOREIGN PATENT DOCUMENTS

WO    WO 9811852 A1 * 3/1998 ............. A45D 34/04

* cited by examiner

*Primary Examiner* — Jennifer C Chiang
(74) *Attorney, Agent, or Firm* — Andrew F. Young, Esq.; Lackenbach Siegel, LLP

(57) ABSTRACT

A liquid dispensing applicator may include a liquid source for housing a liquid. An absorbent member may be adjacent to a proximal end of the liquid source, and may be configured to deliver the liquid to an external surface. An attachment member may secure the absorbent member to the liquid source, and may include a through passage to allow the liquid to flow from the liquid source into the absorbent member. A rigid member may extend outwardly from the attachment member into the absorbent member. A shield member may be positioned adjacent to the attachment member and may extend from the attachment member so as to be positioned within the absorbent member. A capillary tube may be configured to provide fluid communication between the liquid source and the liquid dispenser upon application of pressure to the liquid source.

20 Claims, 11 Drawing Sheets

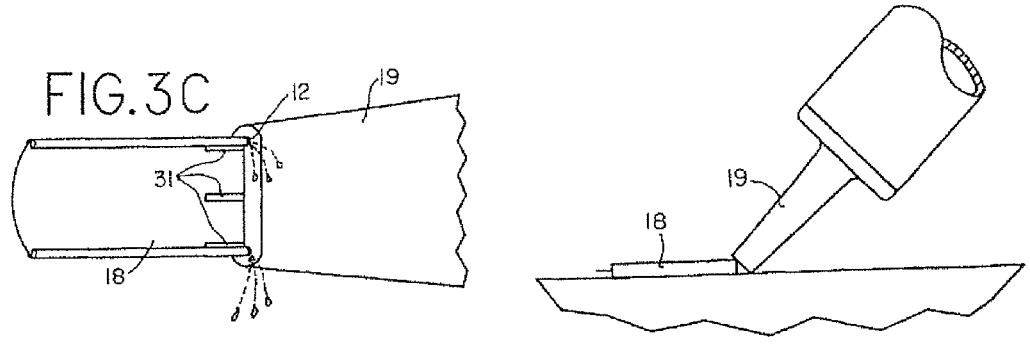
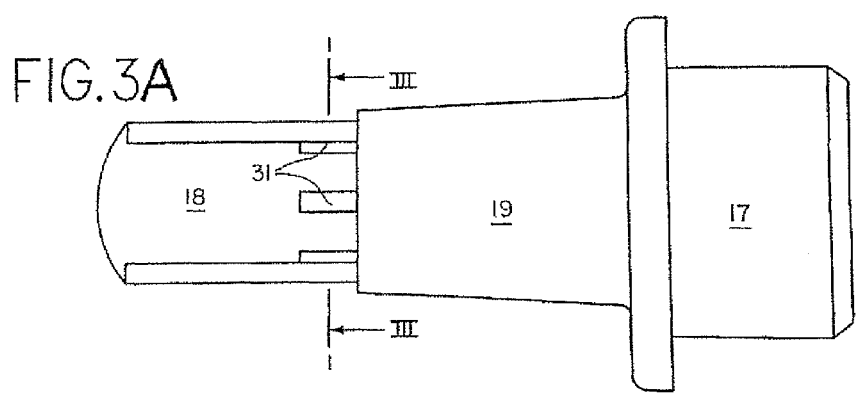

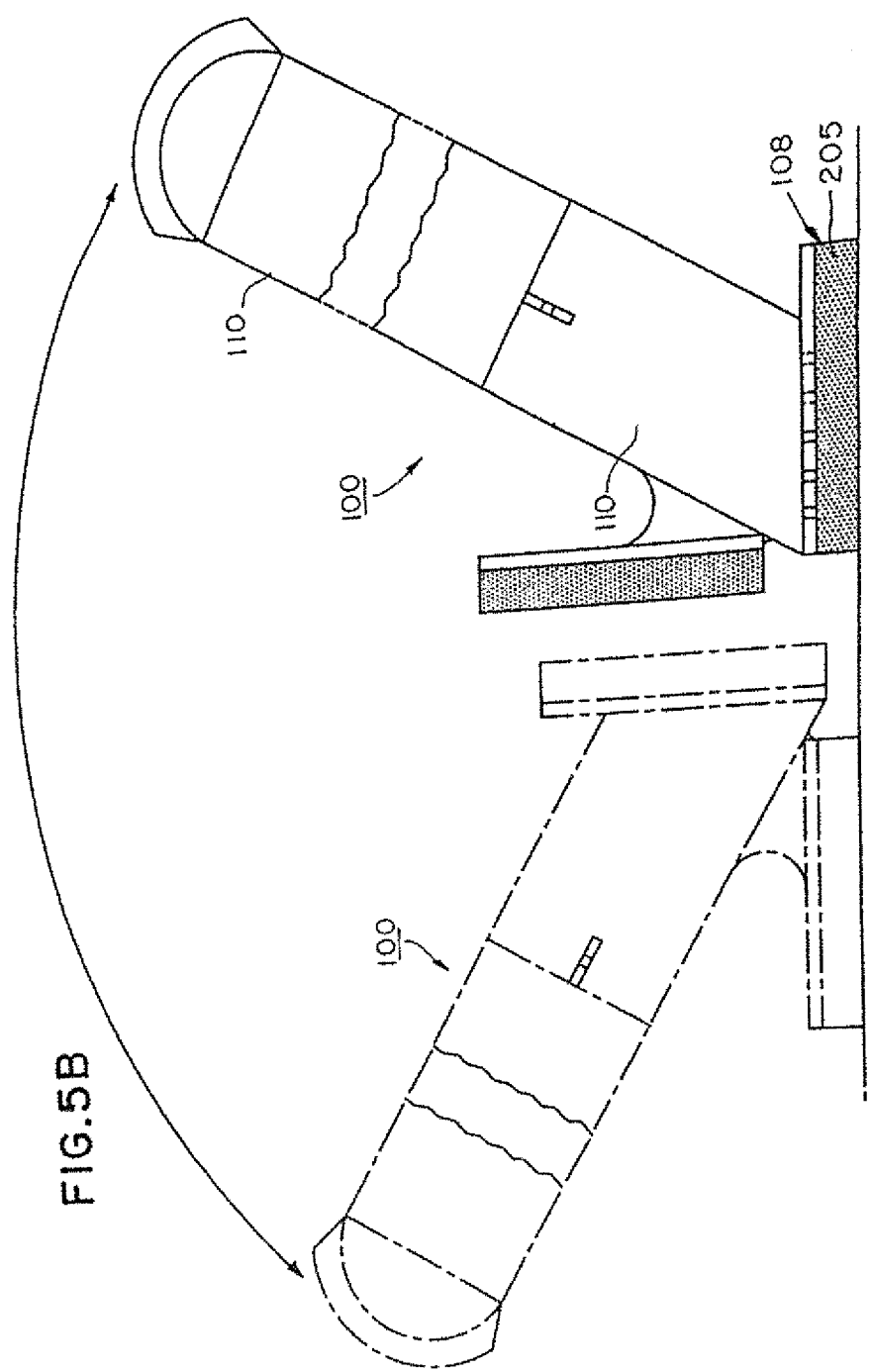

DISPENSING APPLICATOR FOR FLUIDS

REFERENCE TO RELATED APPLICATIONS

This application is a continuation of, and claims priority from, U.S. patent application Ser. No. 13/971,425 for a DISPENSING APPLICATOR FOR FLUIDS filed Aug. 20, 2013, now U.S. Pat. No. 8,926,211 issued Jan. 6, 2015, which in turn is a continuation of and claims to priority from, U.S. patent application Ser. No. 13/485,013 for a DISPENSING APPLICATOR FOR FLUIDS, which is now U.S. Pat. No. 8,608,397 issued Dec. 17, 2013, which in turn is a continuation of and claims to priority from, U.S. patent application Ser. No. 13/102,973 for a DISPENSING APPLICATOR FOR FLUIDS, which is now U.S. Pat. No. 8,215,859, which in turn is a continuation of and claims to priority from, U.S. patent application Ser. No. 12/579,728 for a DISPENSING APPLICATOR FOR FLUIDS, which is now U.S. Pat. No. 7,946,779 issued May 24, 2011, which in turn is a continuation of and claims to priority from, U.S. patent application Ser. No. 11/138,142 for a DISPENSING APPLICATOR FOR FLUIDS, now U.S. Pat. No. 7,614,811 issued Nov. 10, 2009, and incorporates those applications in their entirety herein by reference.

BACKGROUND OF THE INVENTION

1. Field of the Invention

The present invention is directed in general to means for swabbing a surface (i.e., skin) that is gripped by a user at one end and has a sponge or absorbent material at the other end. Further, the present invention is directed to such means for swabbing a surface having a source of a fluid (e.g., disinfectant or medicament) in communication with the sponge or absorbent material. Specifically, the present invention is directed to such a fluid-containing means for swabbing a surface further having means that is fractured or separated for the purpose of allowing the fluid to flow from the fluid source to the sponge or absorbent material.

2. Description of the Related Art

Applicators consisting of a wooden or plastic tube having a bud of cotton on one or both ends, are widely used for numerous purposes, such as the topical application of substances to the human body. A demand exists for a product of this kind which serves not only as an applicator, but also as a container for substances that are to be applied to the human body. To be practical, such a device would have to have a manually frangible portion that can readily be broken, while at the same time being so constructed so as to prevent inadvertent fracture. An applicator of this nature would be useful for numerous purposes.

Prior dispensing applicators allow excess amount fluid to flow too quickly, and the fluid tends to pool on the surface. Depending upon the fluid being dispensed, such pooling can lead to patient discomfort, chemical burns, and even electrical shock if the dispensed fluid comes into contact with electrical leads attached to the patient's body.

Moreover, in prior art dispensing applicators, the dispensed fluid tends to accumulate at the rear-most portion of the absorbent member, which is closest to the fluid source, instead of preferably evenly spreading throughout the absorbent member. As the volume of the dispensed fluid gradually increases at the rear portion of the absorbent member, the fluid starts uncontrollably dripping, thus, causing substantial inconvenience to a user.

A need, therefore, exists for a dispensing applicator overcoming the above-identified drawbacks of the known related art.

A further need exists for a hand-held dispensing applicator that has a simple structure allowing the practitioner to deliver fluid to the surfaces to be treated in a controllable manner.

Another need exists for a dispensing applicator that has an easily actuatable structure requiring minimal application of manual force.

Further, a need exists for a hand-held dispensing applicator that has a structure minimizing uncontrollable distribution of fluid.

ASPECTS AND SUMMARY OF THE INVENTION

In light of the foregoing, the present invention provides a hand-held dispensing applicator comprising a source of fluid, a frangible applicator tip attached to the fluid source, and an absorbent member attached to the frangible applicator tip. When the frangible applicator tip is broken, fluid flows from the source to the absorbent member, whereby the fluid is applied and spread on a surface. Preferably, the fluid is applied and spread on a surface in a controlled amount. Preferably, the fluid source is in the shape of a hollow tube that is integrally formed, as a single piece, from a relatively rigid synthetic resinous material. Preferably, the frangible applicator tip comprises a support element permanently connected to the fluid source, a relatively rigid tongue element extending outwardly of the support element, and a frangible region therebetween. Extending through the support element is a fluid conduit that is open at the end attached to the fluid source and sealed by the tongue element at the end attached to the absorbent member. By deflecting the tongue element relative to the support element, with a force of substantially predetermined magnitude, the frangible region between the tongue and support elements will fracture, thereby permitting fluid to flow from the fluid source through the conduit, and into the attached absorbent member. Preferably, the tongue element comprises ribs for reinforcing the tongue element to resist unintentional breaking of the frangible region. More preferably, the applicator tip comprises a semi-permeable or non-permeable cover disposed around the frangible region to control the speed and direction of the dispersion of the fluid in the absorbent member.

Other aspects, features and advantages of the present invention will be apparent from the following detailed description taken in connection with the accompanying drawings.

BRIEF DESCRIPTION OF THE DRAWINGS

FIG. 3A is a front elevational view of a preferred applicator tip for the dispensing applicator of FIG. 1;

FIG. 3B is a side elevational view of the applicator tip of FIG. 3 wherein the frangible region is broken;

FIG. 3C is a top view of the applicator tip of FIG. 3B wherein apertures are formed in the broken frangible region;

FIG. 5B is a diagrammatic view illustrating two positions of the dispensing applicator of FIG. 5;

DETAILED DESCRIPTION OF THE PREFERRED EMBODIMENTS

Figure 1:
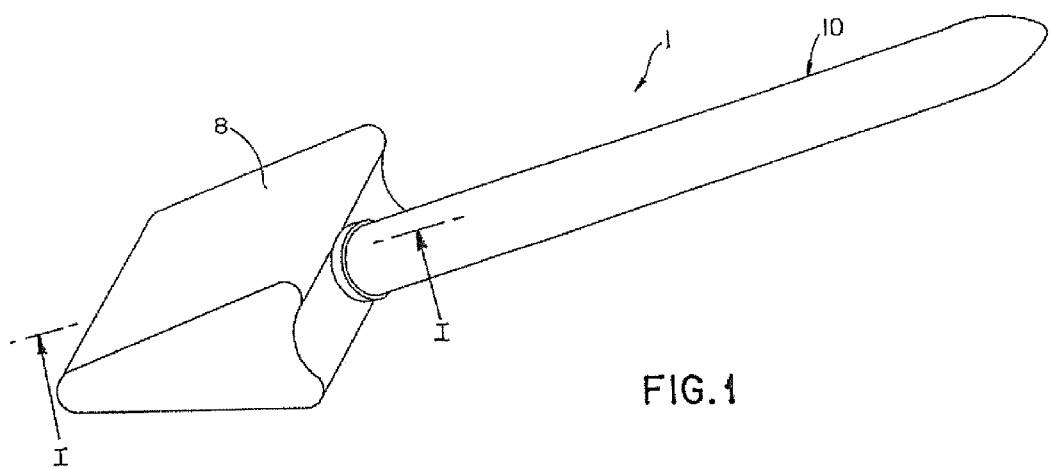
FIG. 1 is a side elevational view of a dispensing applicator according to the present invention.
Figure 2:
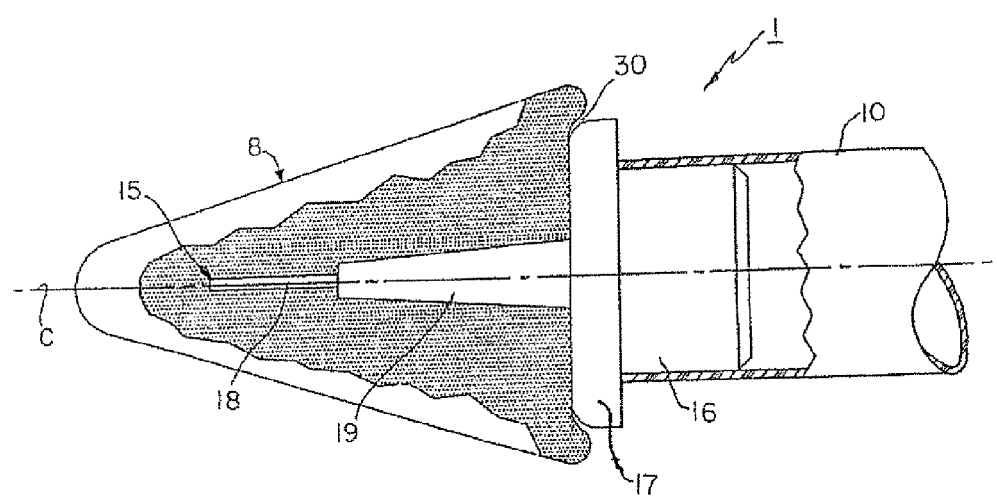
FIG. 2 is a side cross-sectional view of the dispensing applicator of FIG. 1.

Referring to the drawings, FIGS. 1 and 2 in particular, illustrate a dispensing applicator according to the present invention generally indicated as reference numeral 1. Dispensing applicator 1 comprises an absorbent applicator member 8, a fluid source 10, and an applicator tip 15. Absorbent member 8 may be of any suitable shape, such as cubic, cylindrical, or conical, and comprise any suitable absorbent material, such as cotton or sponge. Fluid source 10 may have any suitable shape. As is shown in FIG. 1, fluid source 10 is preferably a hollow, generally cylindrical body. The end of fluid source body located adjacent to absorbent member 8 is preferably sealed thereto at a joint or seam 30, such as by heat sealing, to enclose the fluid substance contained within fluid source body 10. Applicator tip 15 comprises an attachment member 16, an attachment portion 17, and tongue member 18 joined thereto by a tapered frangible region or juncture 19. Tongue member 18 is preferably a flat and broad shape that extends a distance into absorbent member 8, such that tongue member 18 is longer than it is wide (see FIGS. 4A to 4D). It should be noted that the attachment portion 17 is relatively thick adjacent the fluid source body 10, and tapers toward frangible juncture 19. Absorbent member 8 is preferably connected to attachment portion 17 and/or fluid source body 10.

The manner of utilizing dispensing applicator 1 will be self-evident, and simply involves holding the dispensing applicator 1 with the absorbent application member 8 against an application surface. Dispensing applicator 1 is held such that tongue member 18 is at an acute angle (i.e., substantially parallel) to the application surface. Sufficient downward pressure of tongue member 18 against the application surface will deflect tongue member 18 from the central axis c of the fluid source body 10. At a predetermined amount of deflection, the frangible juncture 19 will fracture or break. Fracture of the frangible juncture 19 will desirably be achieved by the application of approximately 0.25 to 5 pounds of force of tongue member 18 against the application surface.

As shown in FIGS. 3B and 3C, breaking frangible juncture 19 will result in the formation of one or more apertures 12 through which fluid from source body 10 may flow into absorbent member 8 (not shown).

In its most preferable form, all portions of the source body 10 will have a wall thickness that is substantially uniform at a value of about 0.005 inch to about 0.025 inch (about 0.127 mm to about 0.635 mm). The source body 10 is preferably made of polypropylene having a density of 0.897 $g/cm^2$ and a flexural modulus of about 150 Kpsi (about 1035 MPa), as determined by ASTM method 790B. The source body 10 is preferably about 6 inches to about 10 inches in overall length, and about 0.25 to about 1.0 inches in diameter, so as to be convenient to grasp and still contain sufficient fluid for a single application.

The applicator tip 15 is about 1 to 3 inches long, and about 0.325 inches in diameter. The frangible juncture 19 will preferably have a thickness of about 0.0005 inch to about 0.002 inch (about 0.013 mm to about 0.050 mm). The one or more apertures 12, which are produced by the fracture of frangible juncture 19, may be of any suitable size, but preferably have a width and height that is substantially correlated to the width and thickness of large ribs 31, 32 (see FIG. 3).

Referring to FIGS. 3A and 3C, tongue member 18 preferably comprises a plurality of reinforcing ribs 31, 32. Due to the reinforcing ribs and the resultant rigidity of tongue member 18, there will be virtually no flex along the length of tongue 18, and an applied force on tongue member 18 will be effectively entirely transferred to and concentrated at frangible juncture 19. The result will be the reliable fracturing of frangible juncture 19, which fracturing results in the formation of one or more apertures 12 of suitable size to permit the fluid within the fluid source body 10 to be discharged therefrom and distributed across a predetermined area of absorbent application member 8 (FIG. 1). As noted above, it will generally be desirable for the material forming fluid source body 10 to be sufficiently thin to permit some compression of fluid source body 10, so as to enable discharge of a liquid therein at a fester rate than would otherwise occur, and/or to promote the flow of the fluid, especially if the fluid is relatively viscous.

Figures 4A, 4B:
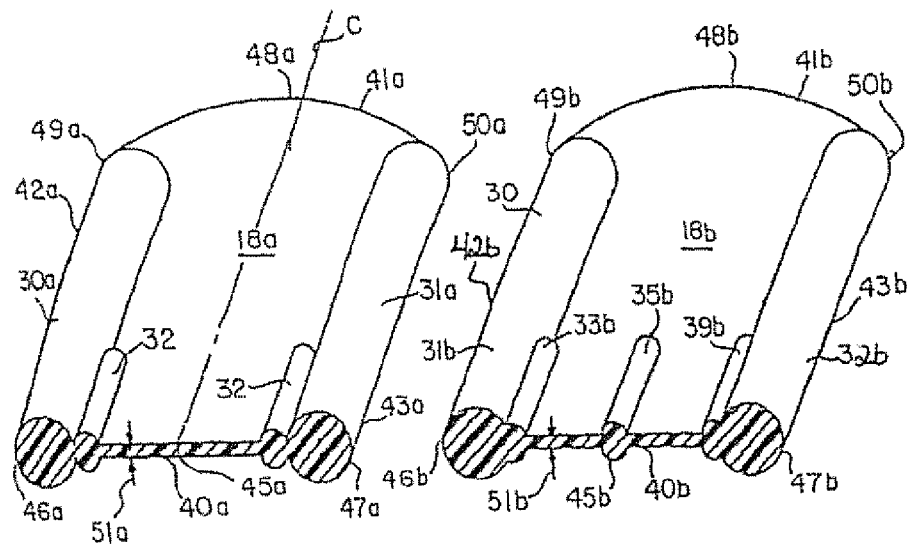
FIG. 4A is a perspective view of a first preferred tongue member for an applicator tip for the dispensing applicator of FIG. 1.
FIG. 4B is a perspective view of a second preferred tongue member for an applicator tip for the dispensing applicator of FIG. 1.

FIG. 4A illustrates a first arrangement of ribs for a tongue 18a. As shown, tongue 18a is rectilinear in shape with a bottom edge 40a, a top edge 41a, and side edges 42a, 43a. Bottom edge 40a is substantially linear with a central point 45a and corners 46a, 47a at which the proximate ends of respective side edges 42a, 43a meet. Top edge 41a is curvilinear with an apex 48a and corners 49a, 50a at which the distal ends of respective side edges 42a, 43a terminate. Central point 45a and apex 48a lie along central axis c. The distance between central point 45a and apex 48a is the length of tongue 18a, while the distance between corners

49a, 50a is the width of tongue 18a, The thickness 51a of tongue 18a is the distance between the top and bottom surfaces thereof. Side edges 42a, 43a each have a respective large rib 31a, 30a extending along the entire length thereof. It is notable that tongue 18a extends a distance beyond the length of the large ribs 31a, 30a, to apex 48a, whereby top edge 41a is not reinforced. Ribs 31a, 30a are each about 3 times the thickness of tongue 18a and about $\frac{1}{5}^{th}$ the width of tongue 18a. Small ribs 32 are disposed directly adjacent to their respective large rib 31a, 30a on the side thereof that is proximate to central axis c. Each small rib 32 extends from bottom edge 40a for a distance that is about $\frac{3}{10}^{th}$ the length of the large ribs 31a, 32a. Each small rib 32 is about 2 times the thickness of tongue 18a and about $\frac{1}{10}^{th}$ the width of tongue 18a.

FIG. 4B illustrates a second arrangement of ribs for a tongue 18b. As shown, tongue 18b is rectilinear in shape with a bottom edge 40b, a top edge 41b, and side edges 42b, 43b. Bottom edge 40b is substantially linear with a central point 45b and corners 46b, 47b at which the proximate ends of respective side edge 42b, 43b meet. Top edge 41b is curvilinear with an apex 48b and corners 49b, 50b at which the distal ends of respective side edges 42b, 43b terminate. Central point 45b and apex 48b lie along central axis c (see FIG. 2). The distance between central point 45b and apex 48b is the length of tongue 18b, while the distance between corners 49b, 50b is the width of tongue 18b. The thickness 51b of tongue 18b is the distance between the top and bottom surfaces thereof. Side edges 42b, 43b each have a respective large rib 31b, 32b extending along the entire length thereof. Large ribs 31b are each about 3 times the thickness of tongue 18b and about $\frac{1}{5}^{th}$ the width of tongue 18b. Small half-ribs 33b, 34b are disposed directly adjacent to their respective large ribs 31b on the sides thereof that are proximate to central axis c. A small rib 35b is disposed along central axis c. Each small half-rib 33b, 34b extends from bottom edge 40b a distance that is about $\frac{3}{10}^{th}$ the length of the large ribs 31b. Each small half-rib 33b, 34b is about 2 times the thickness of tongue 18b and about $\frac{1}{20}^{th}$ the width of tongue 18b. The small rib 35b is about 2 times the thickness of tongue 18b and about $\frac{1}{10}^{th}$ the width of tongue 18b.

Figures 4C, 4D:
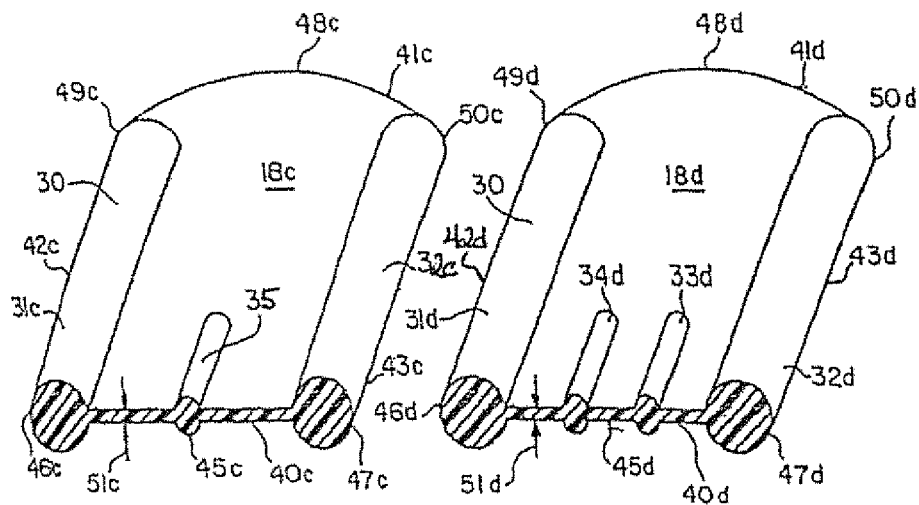
FIG. 4C is a perspective view of a third preferred tongue member for an applicator tip for the dispensing applicator of FIG. 1.
FIG. 4D is a perspective view of a fourth preferred tongue member for an applicator tip for the dispensing applicator of FIG. 1.

FIG. 4C illustrates a third arrangement of ribs for a tongue 18c. As shown, tongue 18c is rectilinear in shape with a bottom edge 40c, a top edge 41c, and side edges 42c, 43c. Bottom edge 40c is substantially linear with a central point 45c and corners 46c, 47c at which the proximate ends of respective side edge 42c, 43c meet. Top edge 41c is curvilinear with an apex 48c and corners 49c, 50c at which the distal ends of respect side edges 42c, 43c terminate. Central point 45c and apex 48c lie along central axis c (see FIG. 2). The distance between central point 45c and apex 48c is the length of tongue 18c, while the distance between corners 49c, 50c is the width of tongue 18c. The thickness 51c of tongue 18c is the distance between the top and bottom surfaces thereof. Side edges 42c, 43c each has a respective large rib 31c, 32c extending along the entire length thereof. Large ribs 31c, 32c are each about 3 times the thickness of tongue 18c and about $\frac{1}{5}^{th}$ the width of tongue 18c. A small rib 35c is disposed along central axis c. The small rib 35c extends from bottom edge 40c a distance that is about $\frac{3}{10}$ the length of the large ribs 31. The small rib 35c is about 2 times the thickness of tongue 18c and about $\frac{1}{10}^{th}$ the width of tongue 18c.

FIG. 4D illustrates a fourth arrangement of ribs for a tongue 18d. As shown, tongue 18d is rectilinear in shape with a bottom edge 40d, a top edge 41d, and side edges 42d, 43d. Bottom edge 40d is substantially linear with a central point 45d and corners 46d, 47d at which the proximate ends of respective side edge 42d, 43d meet. Top edge 41d is curvilinear with an apex 48d and corners 49d, 50d at which the distal ends of respect side edges 42d, 43d terminate. Central point 45d and apex 48d both lie along central axis c (see FIG. 2). The distance between central point 45d and apex 48d is the length of tongue 18d, while the distance between corners 49d, 50d is the width of tongue 18d. The thickness 51d of tongue 18d is the distance between the top and bottom surfaces thereof. Side edges 42d, 43d each has a respective large rib 31d, 32d extending along the entire length thereof. Large ribs 31d, 32d are each about 3 times the thickness of tongue 18d and about $\frac{1}{5}^{th}$ the width of tongue 18d. Spaced apart from each large rib 31d, 32d is a respective small rib 33d, 34d. The small ribs 33d, 34d are spaced apart from each other and evenly spaced from central axis c. The small ribs 33d, 34d are closer to central axis c than to their respective large ribs 31d, 32d. The small ribs 33d, 34d extend from bottom edge 40b a distance that is about $\frac{3}{10}$ the length of the large ribs 31d, 32d. The small ribs 33d, 34d are about 2 times the thickness of tongue 18b and about $\frac{1}{10}^{th}$ the width of tongue 18b. Each small rib 33d, 34d is spaced apart from the central axis c by a distance that is approximately equal to its respective width. The small ribs 33d, 34d are spaced apart from each other by a distance that is approximately equal to 2 times the width of either small rib 33d or 34d. Each small rib 33d, 34d is spaced apart from its respective large rib 31d, 32d by a distance that is approximately equal to 2 times its respective width.

Figure 5A:
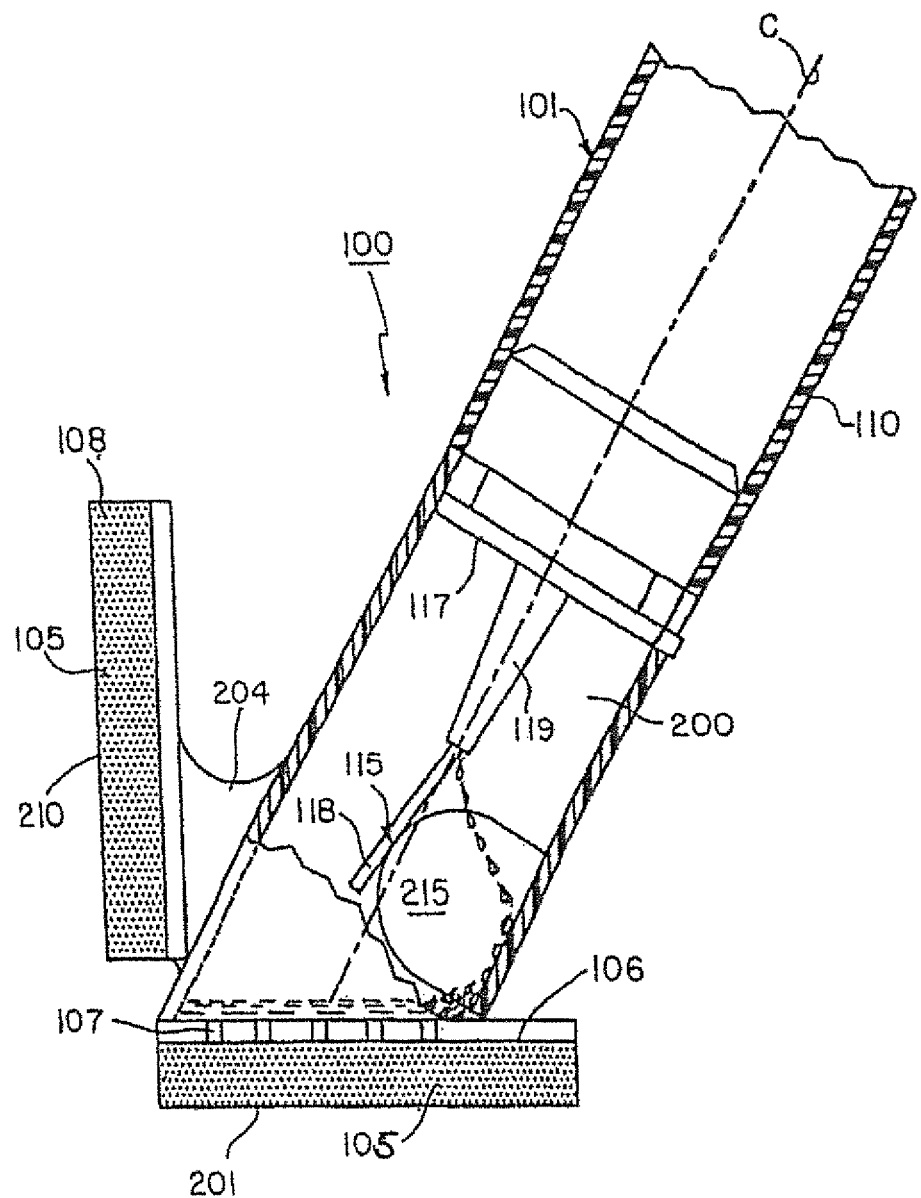
FIG. 5A is a cross-sectional side view of the dispensing applicator constructed in accordance with a further embodiment of the invention.

FIGS. 5A and 5B illustrate a second dispensing applicator 100 according to the present invention. Dispensing applicator 100 comprises an applicator head 108, a source of fluid, which is shown as a hollow, generally cylindrical body 110, and an applicator tip 115, which has an attachment member 117 and tongue member 118 joined thereto by a tapered frangible juncture 119. Fluid source body 110 and applicator tip 115 are respectively identical in form and function to fluid source body 10 and applicator tip 15 described hereinabove in reference to FIGS. 1 through 4D.

In addition, dispensing applicator member 100 is provided with an absorbent swab member 210, and an inwardly projecting ridge-shaped member 215 provided within body 110. A portion of body 110 is adapted to hold and/or support absorbent applicator member 105. As shown, absorbent applicator member 105 is held and supported on a surface 106. Surface 106 is provided with at least one aperture 107, such that the fluid may flow from the interior of body 110 into absorbent applicator member 105, as discussed in further detail herein below. Furthermore, a portion of body 110 is adapted to hold and/or support absorbent swab member 210.

As shown, absorbent swab member 210 is held and supported on a surface 101 that is connected to body 110 by a stock member 204. Absorbent swab member 210 is preferably not in fluid communication with the interior of body 110. Outer surface 201 of applicator member 105 is oriented relative to body 200 such that, when absorbent applicator member 105 is substantially parallel to an application surface (i.e., in contact with the application surface), the central axis c of body 110 forms an angle of about 45° with the application surface, which angle provides a comfortable grip for the user and facilitates the flow of fluid through the interior of body 110 into absorbent application member 105. Similarly, outer surface 201 of swab member 210 is oriented relative to body 200, such that, when absorbent swab member 210 is substantially parallel to an application surface (i.e., in contact with the application surface), the central axis c of body 200 forms an angle of about 30° with the application surface, which angle provides a comfortable grip for the user and allows the user to spread the applied fluid over a relatively large area with relatively less arm movement and/or extension.

The manner of utilizing dispensing applicator 100 involves holding the dispensing applicator 100 with the absorbent application member 105 against an application surface. Downward pressure of applicator 100 against the application surface will displace head 108 upwardly and force ridge-shaped member 215 into contact with tongue member 118. Sufficient upward pressure of ridge-shaped member 215 against tongue member 118 will upwardly deflect the tongue member 118 from the central axis c of the fluid source body 110. At a predetermined amount of deflection, the frangible juncture 119 will fracture or break. Fracture of the frangible juncture 119 will desirably be achieved by the application of approximately 0.25 to 5 pounds of downward force of applicator 100 against the application surface. Breaking frangible juncture 119 will result fluid from fluid source body 110 flowing into head 108. Comparable to breaking frangible region 19 of applicator tip 15, as discussed hereinabove in reference to FIGS. 3A to 3C, breaking frangible region 119 of applicator tip 115 results in the formation of one or more apertures in applicator tip 115 through which fluid from source body 110 may flow into head 108. Thus, in general, applicator tip 15 is comparable in form and structure to applicator tip 115.

Absorbent swab member 210 may be employed for a variety of purposes. Swab 210 may be used to spread a fluid over the application surface after the application member 205 initially applies the fluid. Using swab 210 in this way would be particularly advantageous if the amount of fluid that is desired to cover a relatively large surface area has been inadvertently applied to a relatively small area, which may occur if application member 105 becomes over-saturated with fluid and can no longer effectively regulate the flow rate and amount of fluid being applied. Moreover, swab member 210 may be used to soak up fluid on the application surface, for example, when an excess of fluid has been applied or the fluid has been applied over the wrong area.

As stated above, absorbent swab member 210 is preferably not in fluid communication with the interior of body 200. However, a possible use for swab 210 is applying fluid to a second surface area that is separate and apart from the surface area over which used absorbent application member 205. In the critical interest of avoiding cross-contamination, it is desirable to use the application member 105 over only a single contiguous surface area that should be relatively limited (e.g., the upper front of the torso, instead of the entire front of the torso). Accordingly, after an initial application, any additional fluid in a given dispensing applicator may go wastefully unutilized. Therefore, in another embodiment of absorbent applicator head 108, there is provided at least one aperture (not shown) in surface 101, such that fluid may flow from the interior of body 200 into absorbent swab member 210.

Head 108 may be detachable from fluid body 110. Fluid body 110 may contain an amount of fluid that is greater than is necessary for a given application. Accordingly, after an initial application, any additional fluid in a given dispensing applicator may go wastefully unutilized. Therefore, in another embodiment of applicator 100, fluid body 110 is removably attached to head 108 so that head 108 may be disposed of separately from fluid body 110. If fluid body 110 contains residual fluid after an initial application, other absorbent head may be attached to fluid body 110, thereby allowing the residual fluid to be applied to another application surface.

Figure 6:
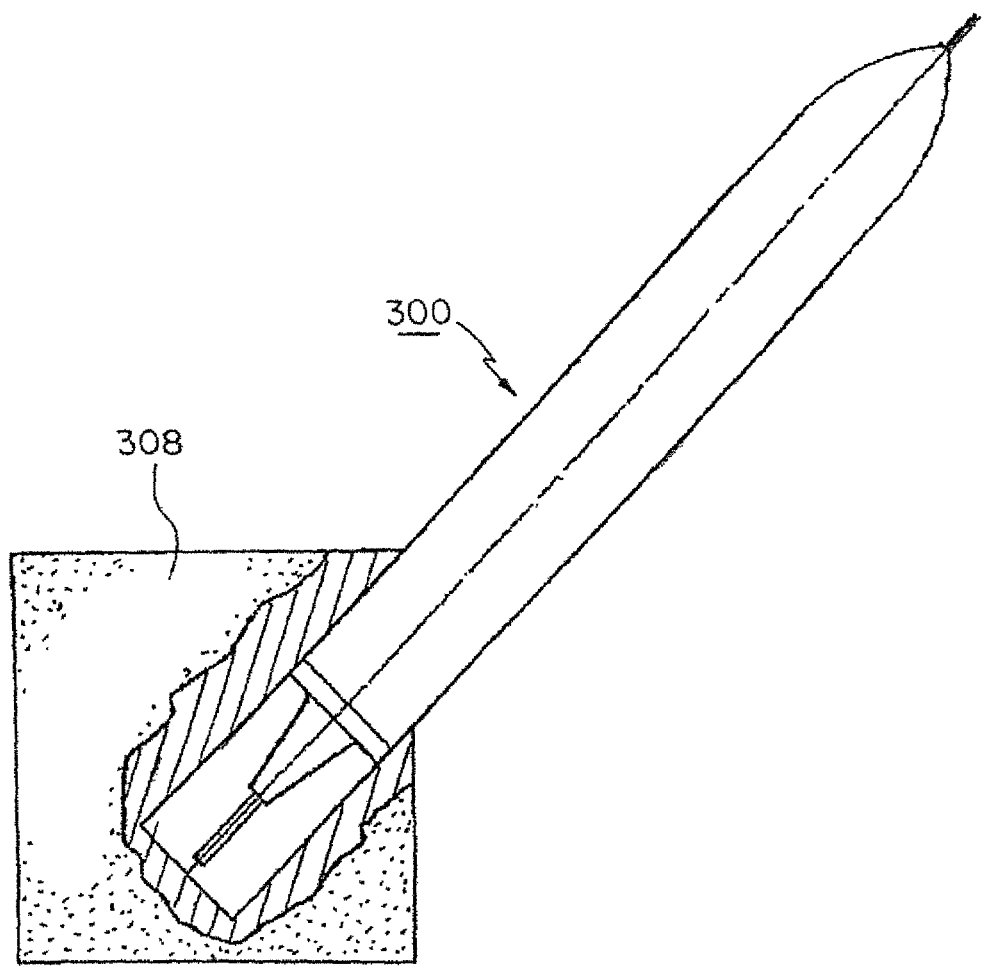
FIG. 6 is a side view of a dispensing applicator structured in accordance with a further embodiment of the present invention and showing a cross-sectional side view of the applicator tip.

Referring to FIG. 6, as stated above, it is desirous to avoid cross-contamination by using a given absorbent applicator over only a single contiguous, relatively limited, surface area. Yet, using a given absorbent application in such a manner will often result in an amount of fluid therein being wasted. Accordingly, a dispensing applicator according to the present invention, generally indicated as reference numeral 300, may be provided with a relatively larger, multi-sided absorbent applicator member 308, such that different sides thereof may be used on different surface areas.

Figure 7:
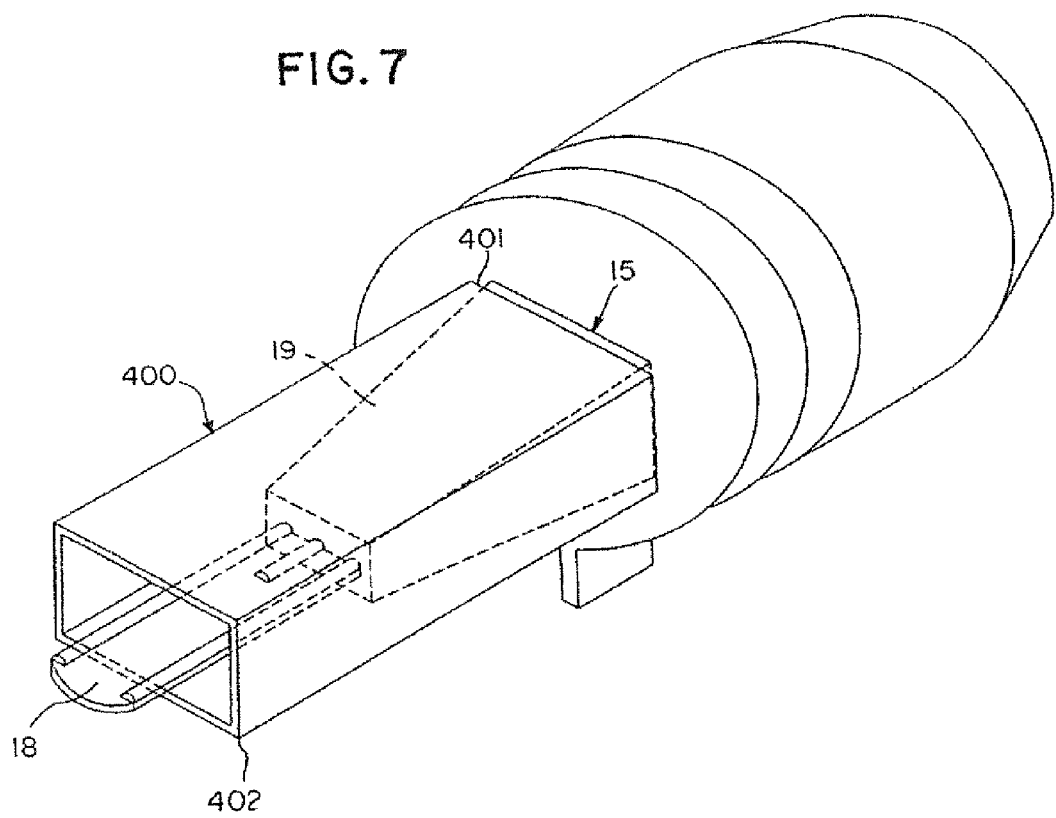
FIG. 7 is a perspective detail view of an applicator tip for use in a dispensing applicator according to the present invention having a semi-cover surrounding the frangible portion to control the speed and direction of the dispersion of the fluid in the absorbent member.

Referring to FIG. 7, there is shown an applicator tip having a semi-permeable or non-permeable cover or shield 400 substantially surrounding frangible juncture 39. The purpose of cover 400 is to control the speed and direction of the dispersion of fluid in a surrounding absorbent member (not shown).

Preferably, a rearward edge 401 of cover 400 will be attached to applicator tip 15. More preferably, rearward edge 401 will be fully sealed around applicator tip 15 without gaps or holes so that fluid may not flow rearward under edge 401. If cover 400 is semi-permeable adjacent to rearward edge 401, fluid may flow rearward through cover 400, but preferably will not flow rearward under edge 401 given the more preferable fully sealed attachment thereof to applicator tip 15. In contrast, a forward or distal edge 402 of cover 400 is preferably free and unattached to applicator tip 15 so that fluid may flow forward under cover 400 substantially without being impeded thereby.

Preferably, cover 400 is formed as a seamless, unitary cylindrical sleeve. Nonetheless, cover 400 may be of any suitable shape and construction. Depending upon its intended function, cover 400 may be semi-permeable or impermeable to fluid. Cover 400 may be made of various materials, including natural and/or synthetic rubbers, thermoplastics (e.g., polyethylene), cellulosic materials or similar fibers (i.e., natural polymeric fibers), and metallic materials. Cover 400 may be a contiguous sheet, a mesh, a felt, or another suitable form, with or without reinforcing fibers and/or seams (i.e., "rip-stop" seams).

Preferably, cover 400 is pliable and flexible so that it does not impede deflection of tongue member 18. In other words, it is preferable that cover 400 does not hinder the breaking of frangible juncture 19.

However, surrounding frangible juncture 19 with a cover 400 having suitable thickness and/or stiffness will provide a level of reinforcement that prevents inadvertent breaking of frangible juncture 19. According, by employing a suitable thick and/or stiff cover 400, tongue member 18 may be provided without reinforcing ribs. Thus, employing cover 400 to reinforce frangible juncture 19 will advantageously simplify production of application tip 15, since tongue member 18 may be molded as a simple flat extension.

Referring again to FIG. 1, a dip mold process may be used to make source body 10, applicator tip 15, or both. The dip molding process begins with preheating of a male mold made from a material having relatively high heat capacity and coefficient of thermal conductivity. This heated mold is then placed in a fluidized bed of meltable particulate resinous material for a time needed to provide a coating of a desired thickness. The mold with melted resinous material is then removed from the fluidized bed, heated a second time and cooled. Finally the tube component is stripped from the mold.

As noted above, it is important for the proper functioning of the applicator that the tube be fabricated from a material that is sufficiently rigid to enable manual fracture of the frangible end portion. If the material is too flexible, deflection of the stem will not produce the desired result. On the other hand, if the material is excessively rigid and brittle, the possibility of an inadvertent fracture will exist, and compression of the body portion to promote flow would be precluded due to the likelihood of cracking, or simply because excess force is required. A variety of synthetic resinous materials may be utilized, the selection of which will be evident to those skilled in the art. The resin must have a sufficiently low melt viscosity to permit coverage of all mold surfaces, and it must produce a nonporous and pinhole-free structure. The polymer will normally be a thermoplastic, and exemplary materials include polypropylene, high density polyethylene, rigid polyvinyl chloride and nylon.

The tongue member of the applicator tip will preferably be elongated to facilitate attachment thereof to the absorbent member 8. However, it is not essential that the tongue member 18 be of any specific shape and, for example, may be rectangular or cylindrical. Regardless of the shape of tongue member 18, it is essential that suitable reinforcing ribs, as described hereinabove, be included to prevent unintentional breaking of frangible portion 19. Moreover, the shape of tongue member 18 will dictate the shape of the orifice formed in applicator tip 15 where the tongue member 18 is separated from attachment member 17. Accordingly, the flow rate and overall amount of fluid applied to an application surface by dispensing applicator 1 is a function of several factors, including the shape and strength of tongue member 18 (and the resulting orifice), the porosity of absorbent member 8, the density of the fluid, and the force employed by the user when breaking frangible portion 19 and pressing absorbent member 8 against the application surface. Determining the optimal flow rate for a given application is well within the ability of one skilled in the art and, therefore, will not be elaborated upon herein.

As stated above, the porous member may be made of any suitable material(s), most notably open cell, soft, and pliant sponge-like foam, that may be, for example, a polyurethane composition. The choice of material will depend largely upon the particular application and the characteristics of tongue member 18 and the fluid held in source body 10.

In its normal form, source body 10 will be of circular cross-section. However, other shapes are also believed to be feasible. The source body 10 may have a square, triangular, or rectangular cross-section, and the shape may indeed be asymmetrical in cross section and of dissimilar shapes at different points along its length. It will be appreciated therefore that, as used herein the term "diameter" is to be construed in a broad sense, so as to be applicable to non-circular elements corresponding to those shown, and to refer to the maximum cross-sectional dimension of the element. Although normally completely hollow, the source body 10 may include appropriate reinforcement elements, such as internal support pillars, to provide adequate overall strength and rigidity, while permitting the source body 10 to have a thinner than would otherwise be possible. Likewise, source body 10 may include a solid portion, for example, to be gripped while breaking frangible portion 19, so that source body 10 will not be prematurely compressed or squeezed, which might result in too much fluid flowing too quickly into absorbent member 8.

Figure 8:
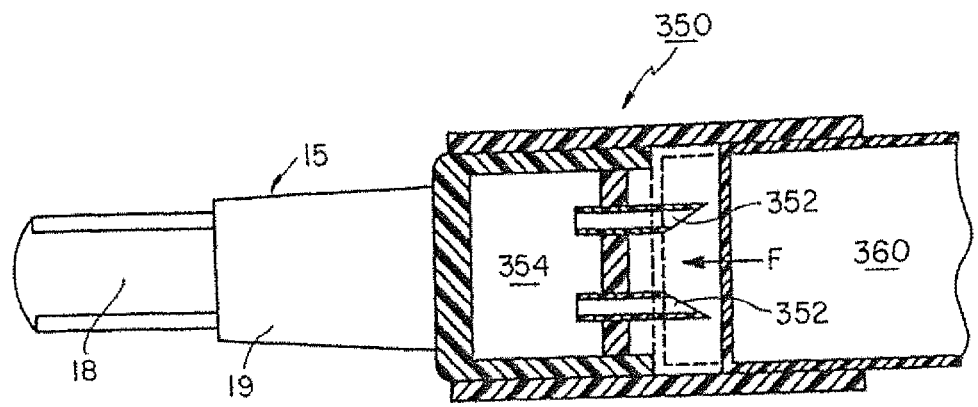
FIG. 8 is a side cross-sectional view of a further aspect of an embodiment of an applicator according to the present invention.

Controlling a rate of dispensing fluid is critical because a) oversaturation of the absorbent member reduces the collecting capability of this member, and b) back flow of the delivered fluid from the distal end towards the proximal end of the absorbent member interferes with the physician's work. Accordingly, FIG. 8 illustrates a further embodiment of the invention directed to a dispensing applicator 350 which is configured to prevent fluid from uncontrollably entering an attachment member 354 that is coupled to tip 15. At least one, but preferably a multiplicity of capillary vessels 352 is provided within the attachment member. Being in fluid communication with a source body 360, vessels 352, by virtue of their cross-section, meter an amount of fluid penetrating into the absorbent member (not shown). Thus, a combination of the openings, which are formed as a result of breaking frangible region 19 and vessels 352, effectively limits oversaturation of the absorbent member.

Figure 9:
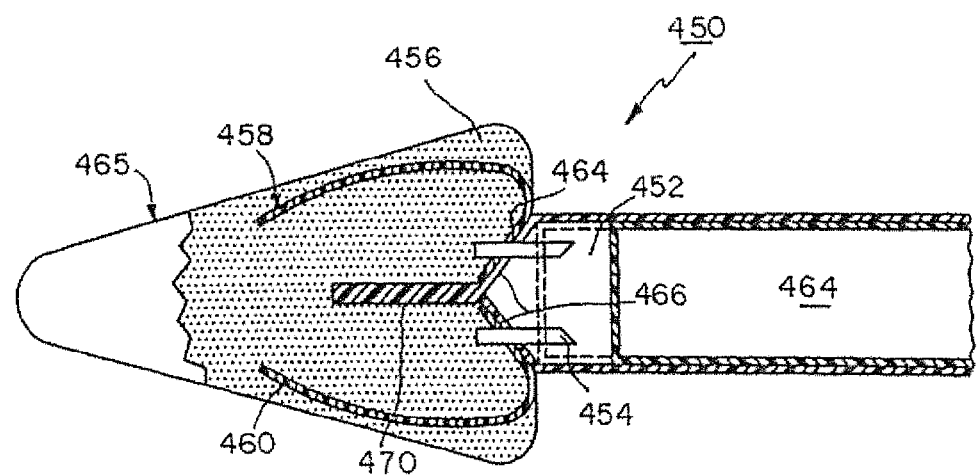
FIG. 9 is a side cross-sectional view of another aspect of an embodiment of the dispensing applicator configured with a collecting and guiding means for minimizing unintended evacuation of fluid via a proximal end of a fluid absorbent member enabling a preferred directional fluid flow.

Still another embodiment of a dispensing applicator 450 is illustrated in FIG. 9. As shown, applicator 450 does not have a frangible structure or region. Instead, an attachment member 452 is provided with at least one or more capillary vessels 454 controllably traverse by fluid from fluid source 464. Vessels 454 project into an applicator tip 465 while penetrating a proximal end of an absorbent member 456. The cross-section of the vessels is selected to provide a metered delivery of fluid.

However, absorbent member 456 can still accumulate an excessive amount of fluid, which will eventually result in a backflow towards the proximal end of the absorbent member and subsequent voluntary evacuation of fluid via this end. To limit or minimize such a possibility, applicator 450 has a flow limiting component or cover or shield 458. Formed within absorbent member 456 and, preferably, sealed to the proximal end thereof, cover 458 is able to collect fluid flowing towards the proximal end of absorbent member 456 and, thus, prevents uncontrollable evacuation of accumulated fluid.

As illustrated, cover 458 is provided with a body having a pair of concave sides 460 whose free or distal ends are spaced from one another at a distance that defines an open exit/entrance for fluid. The bottom portions 464 of cover 458 extend complementary to converging flanks 466 of attachment member 452. Stability of an applicator tip 465 is added by providing the distal end of attachment member 452 with a rib 470. Note that cover 458 does not completely prevent backflow of fluid leaving a space within the absorbent member which is sufficient to amply, but not excessively, wet the surfaces of this member.

Figure 10A:
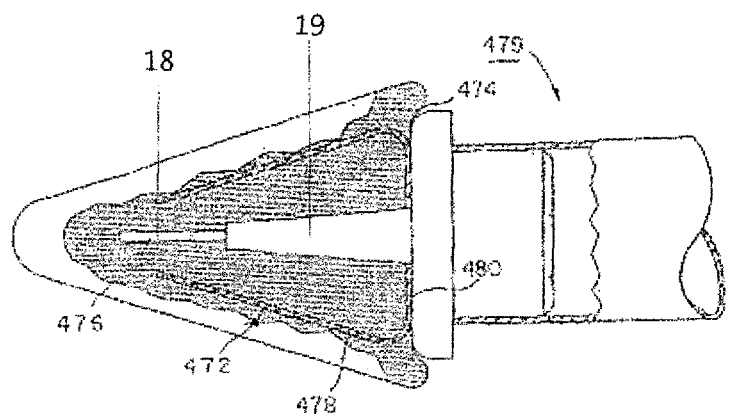
FIGS. 10A and 10B are side sectional and rear sectional views of still another embodiment of the present invention.
Figure 10B:
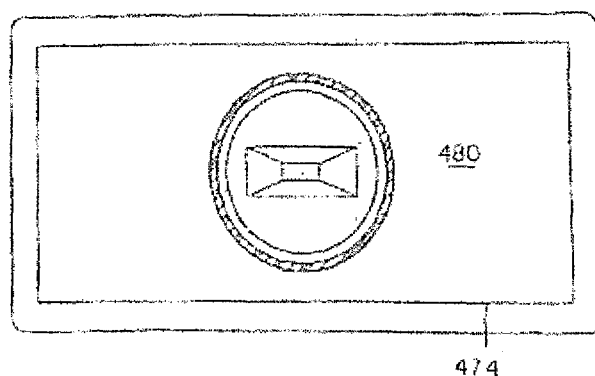

A further embodiment of dispensing applicator 479 is illustrated in FIGS. 10A and 10B. Applicator 479 has a frangible region 19 structured substantially similar to the like configured regions which are discussed in detail above. To prevent uncontrollable evacuation of fluid via a proximal end 474 of an absorbent member 476, applicator 479 has a cover or shield 472 functioning similarly to cover 458 of FIG. 9. However, cover 472 is configured with a pair of rectilinear flanks 478 and a bottom portion 480 that extends parallel to a flat distal end of attachment member 452. The bottom portion of cover 472 allows the frangible region 19 to pass therethrough forming an outlet port (see FIG. 10B) which in turn allows fluid held in source body 10 to pass through the outlet port, through the frangible region 19, and to escape from the aperture formed upon the breaking of frangible juncture 19.

The applicator 479 is formed by inserting cover 472 into and sealing it to the interior of absorbent member 476. The bottom portion 480 lies preferably flush with the proximal end of the absorbent member and is sealingly attached to frangible region 19.

Figure 11A:
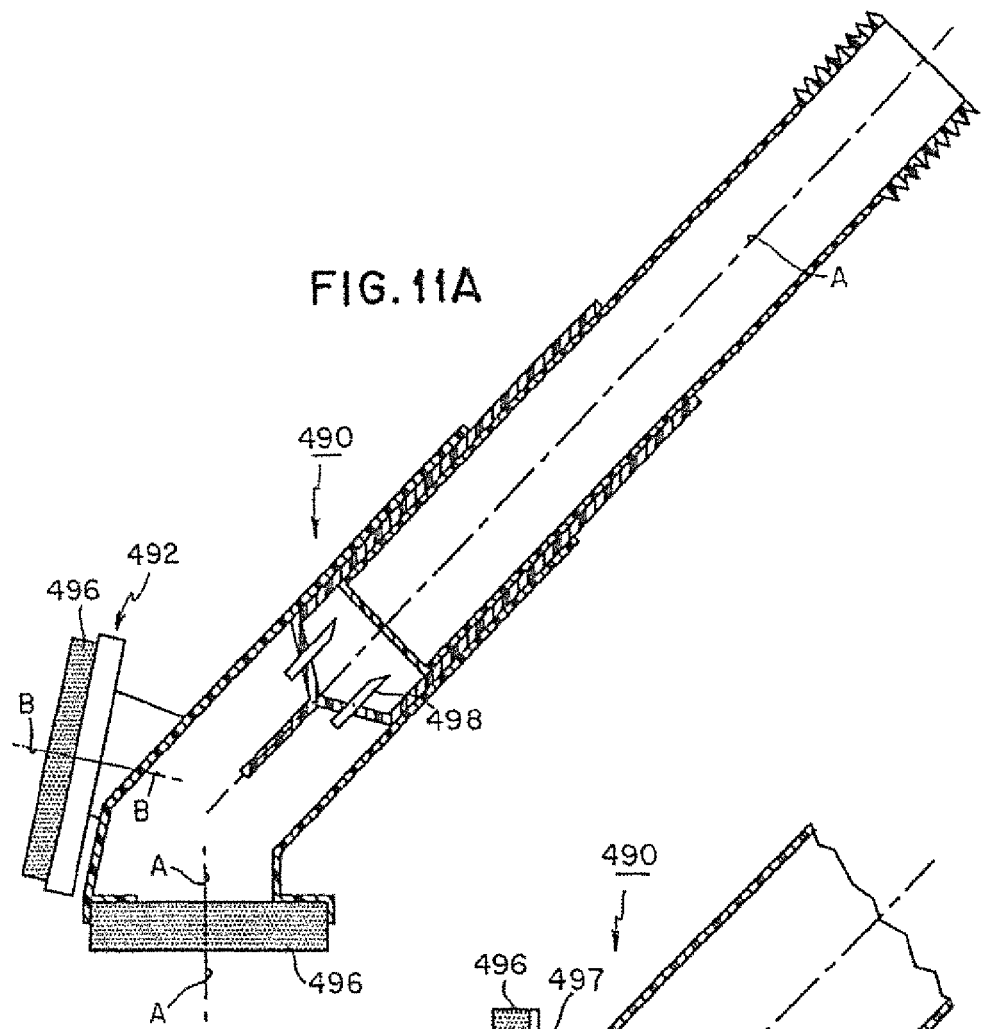
FIG. 11A is a side cross-sectional view of a dispensing applicator according to the present invention.
Figure 11B:
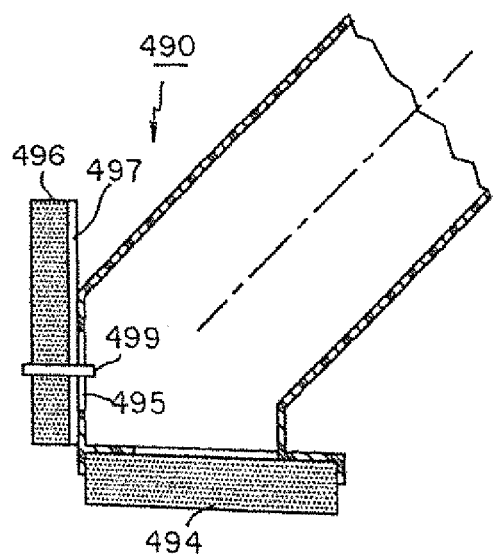
FIG. 11B is a side cross-sectional view of a further aspect of an embodiment of the dispensing applicator according to the present invention.

Embodiments of a dispensing applicator 490 illustrated in FIGS. 11A and 11b are conceptually close to the embodiment illustrated in FIGS. 5A and 5B and include an applicator head 492 which is formed with an absorbent member 494 and a swab member 496. The absorbent and swab members have a center axes A-A and B-B, respectively, which intersect one another forming an angle of about 80-100°.

The difference between the embodiment of FIGS. 5A and 5B and the current one includes utilization of one or more capillary vessels 498 provided instead of the frangible region. While, swab member 496 of FIG. 11A is prevented from fluid communication an interior of a fluid source body, swab member 496 of FIG. 11B is traversed by a capillary tube 499 and has an inner surface 497 in fluid communication with the interior via an opening 495, for the reasons explained above in reference to FIGS. 5A and 5B.

The present invention is primarily directed to a dispensing applicator for the application of liquids to the surface of the head, limbs, and/or body for medical purposes (i.e., pre-surgical disinfection). However, dispensing applicators according to the present invention may be used in a wide variety of purposes and environments. For example, a dispensing applicator according to the present invention can be used for application of lubricant(s) or adhesive(s). The range of sizes can also vary widely, as long as the several wall thicknesses are controlled appropriately to afford the desired functional characteristics discussed herein. It should also be appreciated by those of skill in the art that the fluid reservoirs, in selected embodiments, are flexibly bounded and allow an operator to control volumetric application based on the amount of pressure applied to the exterior of the reservoir. As a consequence of this design, it should also be recognized by those of skill in the art, that an operator releasing a compressed reservoirs, may partially suction released fluid back into the reservoir and minimize pooling.

It will be understood that the present invention may be embodied in other specific forms without departing from the spirit or central characteristics thereof. The present examples and embodiments, therefore, are to be considered in all respects as illustrative and not restrictive, and the invention is not to be limited to the details given herein.

What is claimed is:

1. A liquid dispensing applicator, said applicator comprising:
   (a) a liquid source for housing a liquid, said source having a closed distal end and a proximal end;
   (b) an absorbent member for dispensing said liquid, said absorbent member having a distal tip end and a proximal base end, and said absorbent member being adjacent said proximal end and configured to deliver said liquid to an external surface;
   (c) an attachment member for insertion into said proximal end of said liquid source to secure said absorbent member to said liquid source, said attachment member having a through passage to allow said liquid to flow from said liquid source into said absorbent member;
   (d) a rigid member extending outwardly from said attachment member into said absorbent member;
   (e) a shield member positioned adjacent to said attachment member and extending from said attachment member so as to be positioned within said absorbent member; and
   (f) a capillary tube configured to provide fluid communication between said liquid source and said liquid dispenser upon application of pressure to said liquid source.

2. The liquid dispensing applicator according to claim 1, wherein said shield member is configured with a pair of concave sides to guide said liquid flowing from said capillary tube toward said distal tip end of said absorbent member.

3. The liquid dispensing applicator according to claim 1, wherein said shield member is formed from a fluid-resistant material selected from the group consisting of natural rubber, synthetic rubber, thermoplastic, cellulosic material, similar fiber, and metal.

4. The liquid dispensing applicator according to claim 1, wherein said shield member has a bottom juxtaposed with a proximal base end of said absorbent member and a pair of flanks converging towards said distal tip end of said absorbent member, said flanks being spaced apart and terminating at a distance from said distal tip end so as to allow said liquid to propagate across said absorbent member toward said distal tip end.

5. The liquid dispensing applicator according to claim 1, wherein said rigid member extends outwardly from said attachment member toward said distal tip end to guide dispersion of said liquid through said absorbent member in a direction toward said distal tip end.

6. The liquid dispensing applicator according to claim 1, wherein said closed distal end is closed with a closure cap.

7. The liquid dispensing applicator according to claim 6, wherein said closure cap is secured to said distal end of said source by a mechanism selected from the group consisting of snap fit and threading.

8. The liquid dispensing applicator according to claim 1, wherein said attachment member is attachable to said proximal end of said source with a threaded interface therebetween.

9. The liquid dispensing applicator according to claim 1, wherein said shield member is semi-permeable.

10. A liquid dispensing applicator, said applicator comprising:
    (a) a container of liquid comprising a body having a closed distal end and a proximal end; and
    (b) a liquid dispensing arrangement for dispensing said liquid from said container onto an external surface, said liquid dispensing arrangement comprising:
       (i) an absorbent member positioned adjacent said proximal end of said body, said absorbent member for receiving said liquid from said container and dispensing said liquid onto said external surface;
       (ii) an attachment member connected with said proximal end of said body to secure said absorbent member to said body;
       (iii) a guide member connected with said attachment member and extending from said attachment member into said absorbent member;
       (iv) a capillary tube configured to provide fluid communication between said container and said absorbent member upon application of pressure to said container; and
       (v) a rigid member extending outwardly from said attachment member into said absorbent member;
    wherein said attachment member has a through passage to allow said liquid to flow from said container to said absorbent member.

11. The liquid dispensing applicator according to claim 10, wherein said guide member is configured with a pair of concave sides to guide said liquid flowing from said capillary tube toward said distal tip end of said absorbent member.

12. The liquid dispensing applicator according to claim 10, wherein said guide member is formed from a fluid-resistant material selected from the group consisting of natural rubber, synthetic rubber, thermoplastic, cellulosic material, similar fiber, and metal.

13. The liquid dispensing applicator according to claim 10, wherein said guide member has a bottom juxtaposed with a proximal base end of said absorbent member and a pair of flanks converging towards said distal tip end of said absorbent member, said flanks being spaced apart and terminating at a distance from said distal tip end so as to allow said liquid to propagate across said absorbent member toward said distal tip end.

14. The liquid dispensing applicator according to claim 10, wherein said rigid member extends outwardly from said attachment member toward said distal tip end to guide dispersion of said liquid through said absorbent member in a direction toward said distal tip end.

15. The liquid dispensing applicator according to claim 10, wherein said closed distal end is closed with a closure cap.

16. The liquid dispensing applicator according to claim 15, wherein said closure cap is secured to said distal end of said source by a mechanism selected from the group consisting of snap fit and threading.

17. The liquid dispensing applicator according to claim 10, wherein said attachment member is attachable to said proximal end of said source with a threaded interface therebetween.

18. The liquid dispensing applicator according to claim 10, wherein said guide member is semi-permeable.

19. A liquid dispensing applicator, said applicator comprising:
an absorbent member having proximal and distal ends, said proximal end in fluid communication with a source of liquid;
a guide located within said liquid absorbent member and extending between said proximal and distal ends, said guide being configured with at least a pair of concave sides to control voluntary evacuation of said liquid through said liquid absorbent member;
a substantially rigid member extending outwardly within said absorbent member towards said distal end thereof; and
at least one capillary tube configured to provide fluid communication between said liquid source and said absorbent member;
wherein said absorbent member is configured to dispense a liquid to an external surface.

20. The liquid dispensing applicator according to claim 19, wherein said rigid member extends outwardly from said proximal end of said absorbent member toward said distal end to guide dispersion of said liquid through said absorbent member in a direction toward said distal end.

* * * * *